United States Patent [19]

Gilliam et al.

[11] 4,205,747
[45] Jun. 3, 1980

[54] LENS STORAGE DEVICE

[75] Inventors: James J. Gilliam, Altadena; James G. Fetz, La Verne, both of Calif.

[73] Assignee: Cilco, Inc., Huntington, W. Va.

[21] Appl. No.: 939,382

[22] Filed: Sep. 5, 1978

[51] Int. Cl.² .................... A45C 11/04; G02C 07/04
[52] U.S. Cl. .................................. 206/5.1; 3/13; 350/242
[58] Field of Search .................. 206/5.1; 3/13; 73/431; 351/160 R, 86; 350/242

[56] References Cited

U.S. PATENT DOCUMENTS

| 3,510,196 | 5/1970 | Beer | 350/242 |
| 3,524,455 | 8/1970 | Haagesteger | 206/5.1 |
| 3,997,049 | 12/1976 | Sherman | 206/5.1 |

FOREIGN PATENT DOCUMENTS 2305749  11/1976  France .......................... 206/5.1

*Primary Examiner*—Herbert F. Ross
*Attorney, Agent, or Firm*—Lyon & Lyon

[57] ABSTRACT

An improved structure for storing lenses, including storage during shipment, is disclosed. The device comprises a cylindrical upper portion with a knurled flange at the top thereof, together with an interlocking coaxially cylindrical lower portion having a knurled flange at the bottom thereof. A central bore extending through each of the cylindrical portions permits inspection and irrigation of the lens while in the device, but maintains the lens in a substantially fixed position, thereby avoiding scratches. The device is specially suited to storage of anterior chamber intraocular lenses.

8 Claims, 4 Drawing Figures

LENS STORAGE DEVICE

FIELD OF THE INVENTION

The present invention relates generally to lens storage devices, and more particularly to storage devices suitable for use with intraocular lenses.

BACKGROUND OF THE INVENTION

Storage devices for intraocular lenses typically have been adapted from the lens cases used with contact lenses. A typical device for storing contract lenses generally has a concave lower portion which forms a reservoir for holding a fluid suitable for use with the contact lens, together with the lens itself. A press-fit cap is usually placed thereover, which may be connected to the base portion by means of a tab or other connector. The cap seals the reservoir to prevent loss of the fluid, and neither the cap nor the reservoir are vented.

This design suffers from several limitations which limit its usefulness as an intraocular anterior chamber lens package. Intraocular lenses are typically stored and shipped in a dry environment, and thus it becomes important that the lens storage device be configured to prevent scratching the lens. Therefore a conventional contact lens package is generally unacceptable for use with intraocular lenses, since scratching could occur when the lens is placed in or removed from the package. If a conventional package is used, scratching is also likely to occur simply during transportation of the lens since the concave lower portion is typically substantially larger than the lens itself, permitting the lens to shift during movement of the package.

Additionally, intraocular lenses must typically be inspected before surgical implantation in the eye, and frequently are irrigated prior to implantation. Neither of these tasks is conveniently accomplished with a conventional intraocular lens store device. Inspection of the lens requires that it be removed from the package, which often requires that the lens be re-sterilized. Irrigation requires further handling, which is frequently difficult in view of anterior chamber lens size and the fact that sterility of the lens should be maintained. In addition, conventional lens cases are typically difficult to open in the operating theater.

Nevertheless, lens packages such as described above for use with contact lenses have been generally provided for use with intraocular lenses. In view of the disadvantages associated with such a lens package, it is apparent that there has been a need for a storage device, suitable for use during shipping, which eliminates at least some of these problem areas.

SUMMARY OF THE INVENTION

The present invention eliminates or substantially improves upon each of the foregoing areas of difficulty with existing intraocular lens cases and is particularly suited to use with anterior chamber intraocular lenses such as that disclosed in U.S. patent application Ser. No. 901,819 filed May 1, 1978. A lens storage device according to the present invention provides a lower lens supporting portion together with an interlocking cap whereby the position of the lens is fixed between the cap and the lower portion once the cap is in place.

Flanges are provided on both the upper and the lower portion suitable for easily gripping the package. A central bore is provided through the lens supporting the cap portions to permit irrigation of the lens with a sterilizing gas. The bore also permits examination of the ocular portion of the lens under a microscope without removal of the lens from the storage device.

One object of the present invention is to provide an improved lens storage device.

A further object of the present invention is to provide an improved intraocular lens storage device whereby the lens may be inspected without removal from the storage device.

Still, another object of the present invention is to provide a lens storage device whereby the lens may be transported without fear of scratching.

A still further object of the present invention is to provide a lens storage device whereby the lens may be irrigated or sterilized without removal from the storage device.

Still another object of the present invention is to provide a lens storage device whereby the package may be readily opened by one wearing surgical gloves.

These and other objects of the present invention will be better understood from the following detailed description of the invention, taken together with the appended figures in which FIG. 1 shows an exploded perspective view of the lens case;

DESCRIPTION OF THE PREFERRED EMBODIMENTS

Figure 1:
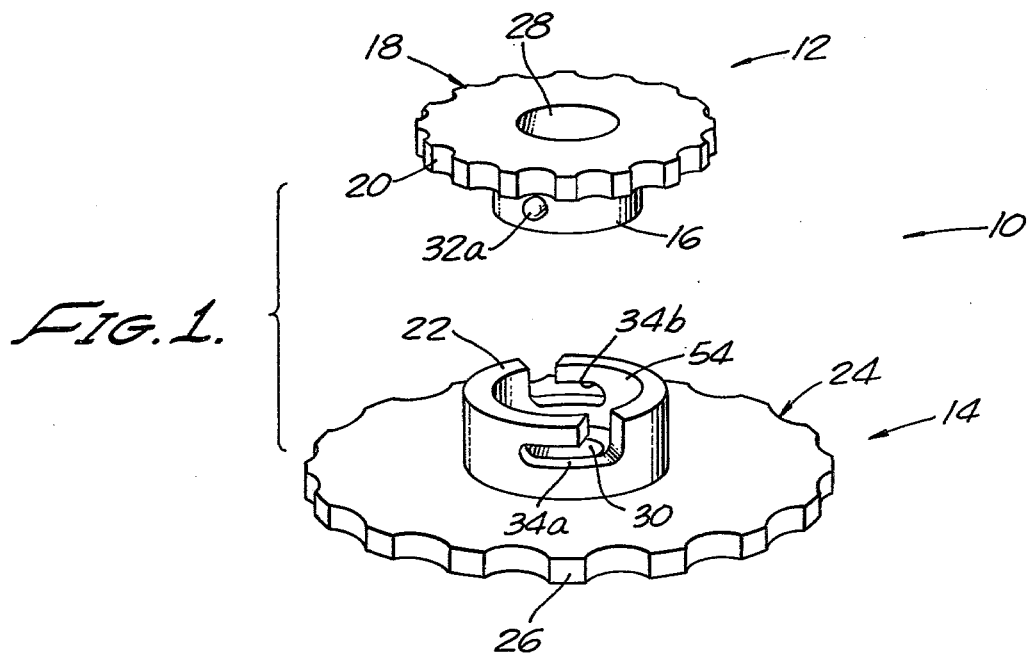

Referring first to FIG. 1, which illustrates an exploded perspective view of a lens storage device according to the present invention, a storage device is indicated at 10 which comprises a cover 12 and a base 14. The cover portion 12 has a cylindrical center portion 16 to which is attached at the top thereof a flange 18. The flange 18 may be provided with a knurled outer edge 20. The base portion 14 similarly has a cylindrical center portion 22 and a flange 24 connected at the bottom thereof. As with the flange 18 of the upper portion 12, the outer perimeter 26 of the flange 24 may be serrated or knurled. A central bore 28 extends through the cover 12, and similarly a central bore 30 extends through the base portion 14, as better seen from FIG. 4.

Figure 4:
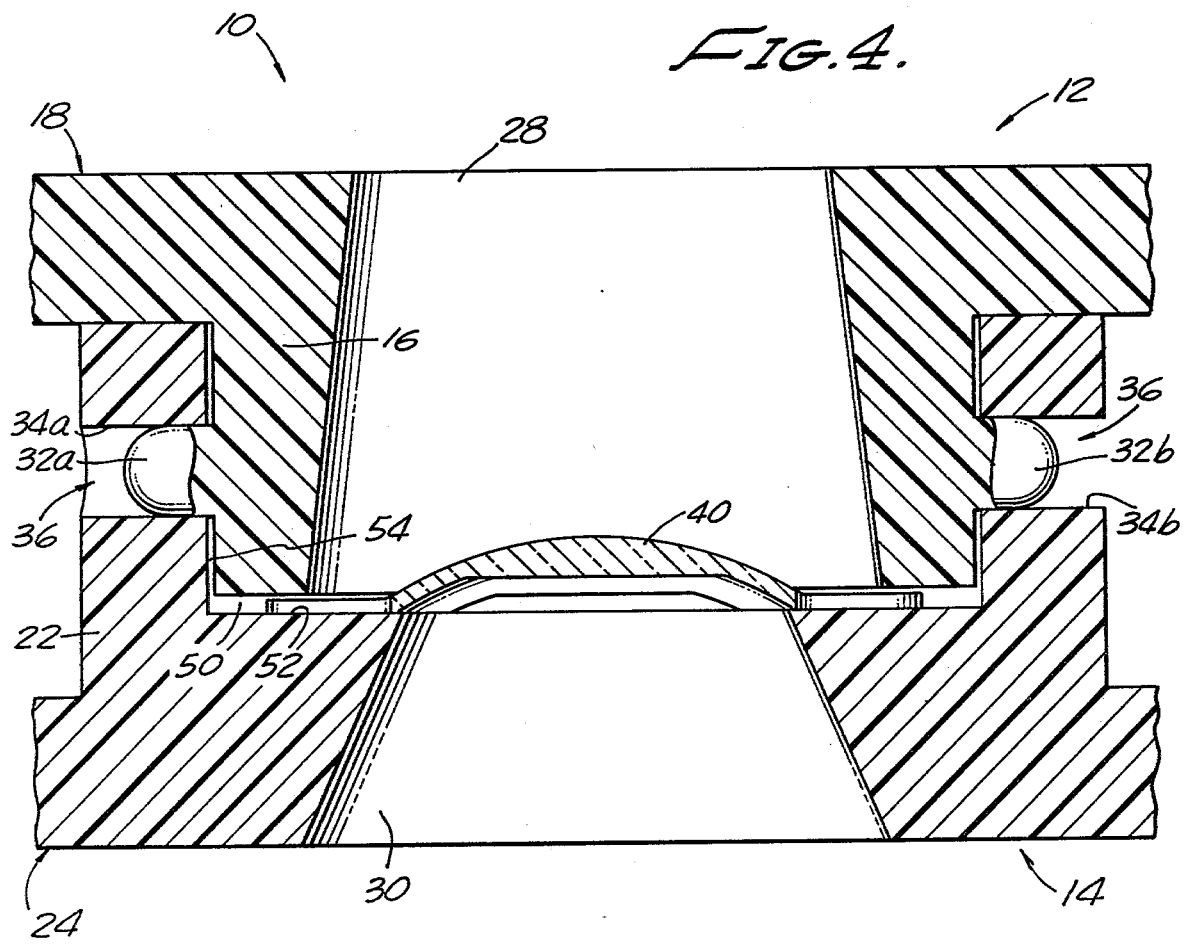
FIG. 4 shows a cutaway side view taken along the section lines shown in FIG. 2.

Also, the cover 12, on the cylindrical center portion 16 thereof, is provided with a pair of pins 32(a) and 32(b), better seen in FIG. 4. As can be better appreciated from FIGS. 2-4, the pins 32 (a)-(b) cause the cover 12 to interlock with the base portion 14 by means of a pair of cam slots 34(a) and 34(b) therein, thereby forming a bayonet clamp 36.

Figure 2:
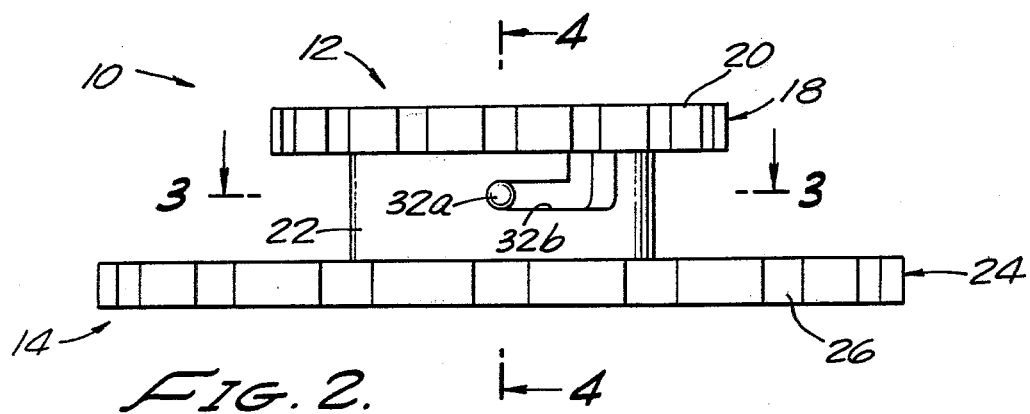
FIG. 2 shows a side view of the lens case.

Referring to FIG. 2, the storage device 10 is shown with cover 12 locked in the interconnected position with the base 14. Thus, the pin 32(a) is twisted into the locked position in the cam slot 34(a). The corresponding pin 32(b) is similarly interconnected with the slot 34(b), on the other side of the device 10. The flange 18 and flange 24 may be of different diameters, also as shown in FIG. 2, although the present invention is not restricted to a particular relationship of diameters of the flanges. Further, the knurled perimeters of each flange are not in all instances required.

Figure 3:
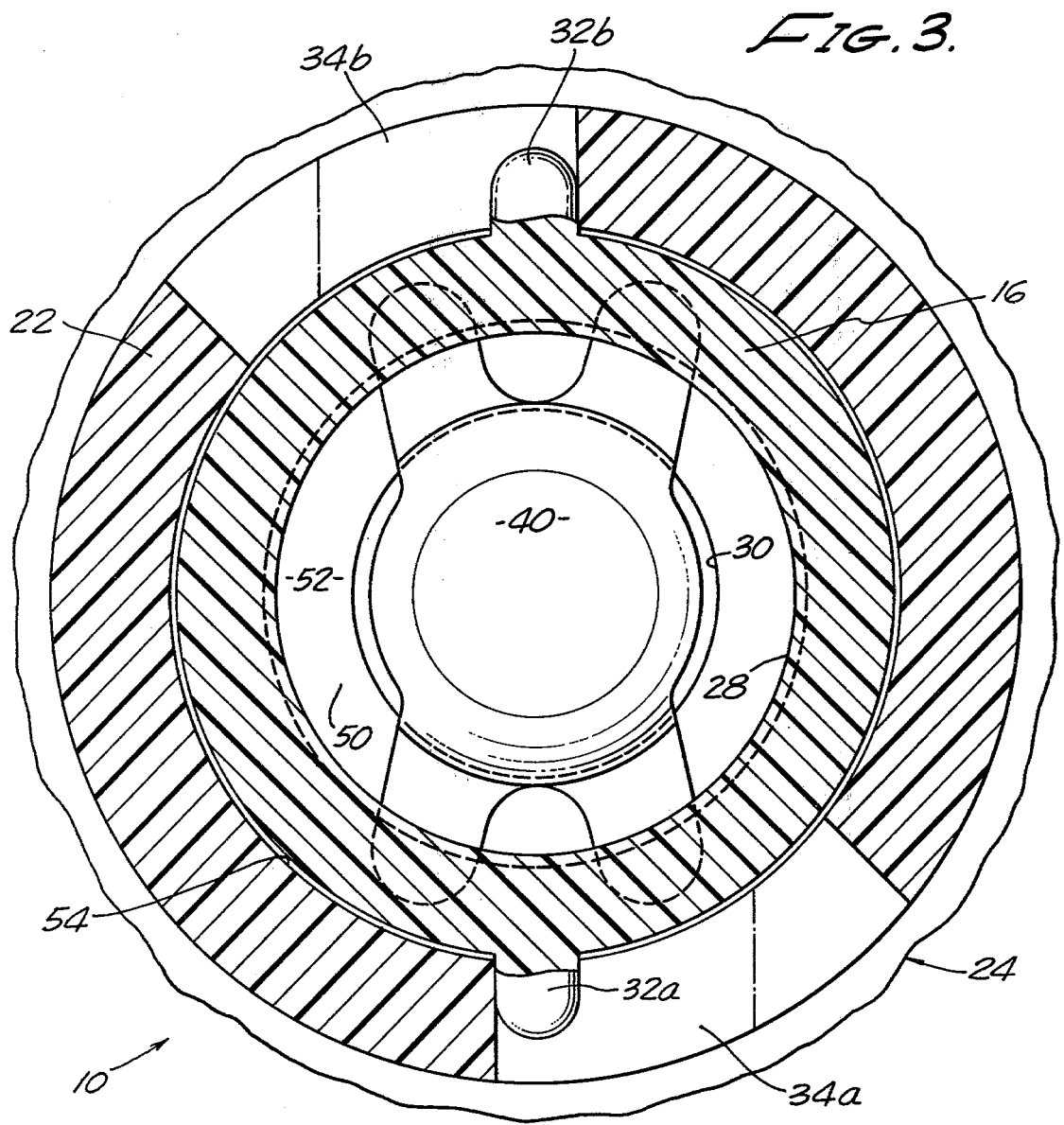
FIG. 3 shows a cutaway plan view of the lens case.

Turning to FIGS. 3 and 4, there are shown therein sectioned views of the lens device 10 taken, respectively, along section lines 3—3 and 4—4 as shown in FIG. 2. In both FIGS. 3 and 4 the flange portions of the base portion 15 and cover 12 have been broken away to permit showing in greater detail the central portions of the device 10.

A lens 40, and more particularly an intraocular anterior chamber lens as described in U.S. patent application Ser. No. 901,819 filed May 1, 1978, is shown in place of the base portion 14 of the device 10. More specifically the lens 40 fits within a cavity 50 bounded by a surface 52 and wall 54 in the base 14, and rests on the surface 52 in the cavity 50. The diameter of the cavity preferably allows the lens 40 to freely clear the inner wall 54 of the cylindrical center portion 22 of the base 14.

The central bore 30 extends through the base 14 and connects with the cavity 50, thereby exposing the underside of the lens 40 and permitting irrigation and inspection of the lens as will be better understood hereinafter. The bore 30 may be seen from FIGS. 3 and 4 to slope slightly inward from the bottom of the base 14 to the surface 52. While such sloping is preferable and permits better irrigation of the lens, it is not required for all applications of the present invention and other arrangements of the bore 32 are within the scope of the present invention. Also, the diameter of the bore 30 need only be of such size as to maintain the lens when properly positioned in the cavity 50.

In both FIGS. 3 and 4, the cover 12 is shown fitted into the base 14 by means of the bayonet clamp 36, which are comprised of the pins 32 (a)-(b) and cam slots 34 (a)-(b). The cylindrical portion 16 of the cover 12 can be seen to slightly frictionally engage the lens 40, thereby maintaining the lens 40 substantially in a fixed position between the cover 21 and base 14 within the cavity 50. The slight frictional engagement should be such as to fix the position of the lens in the cavity, but not such as to scratch the lens. A slight clearance may be substituted, in some instances for the slight frictional engagement. In addition, and similar to the bore 30 in the base 14, a bore 28 extends through the cover 12, connecting to the cavity 50. The bore 28 slopes slightly inward from the bottom to the top of the cylindrical center portion 16 although this particular arrangement is not required as discussed above.

Because of the bores 28 and 30, the lens 40 is exposed on both the upper and lower sides. This permits the lens to be inspected under the microscope without removal from the package, and also permits the lens to be irrigated prior to removal. From FIG. 3 the lenticular portion of the lens 40 can be seen to be of approximately the same or a slightly larger diameter as the bores 28 and 30, although this relationship is not critical. The lens 40 is supported in the device 10 by its haptic feet, thus leaving the lenticular portion thereof unobstructed and free of the possibility of being scratched or otherwise marred. The bore 28 is preferably dimensioned so that any sideslip of the lens 40 within the cavity 50 will not bring the lenticular portion of the lens 40 into contact with the cover 12.

Having fully described a preferred embodiment of the invention, it is to be understood that numerous alternatives and equivalents which do not depart from the present invention will be apparent to those skilled in the art, given the teaching herein, and are intended to be included within the scope of the present invention.

We claim:

1. A lens storage device for storing a single intraocular lens having a cylindrical first portion having a cavity therein and a central bore therethrough to expose to view at least a substantial amount of the lenticular portion of the lens, said cavity being adapted to receive the intraocular lens, and a cylindrical second portion adapted to fit within said cavity in said first portion and to interlock therewith to maintain the lens within said cavity, said cylindrical second portion having a central bore therethrough which communicates with said central bore in said first portion to provide an unobstructed optical path through at least a substantial amount of the lenticular portion of the lens.

2. An intraocular lens storage device having a base including a cylindrical center portion having a cavity therein for receiving a single intraocular lens, and a bore extending through the center thereof, a cover including a cylindrical center portion of an outside diameter substantially the same as the diameter of said cavity in said base and extending into said cavity sufficiently to prevent the lens placed in said cavity from moving, said cover having a bore extending through the center thereof in communication with said bore in said base to expose at least part of both sides of the lens.

3. A lens package comprising a first cylindrical portion including a cavity adapted to receive an intraocular lens and having a bore extending through the center thereof, a second cylindrical portion adapted to fit within the cavity of said first portion for fixing the position of the lens therebetween, said second portion having a bore extending through the center thereof which communicates with said bore through said first portion to expose at least part of both sides of the lens, and locking means integral with said first and second portions to affix said first portion to said second portion.

4. An intraocular lens package comprising a base having a substantially cylindrical center portion and a flange at the bottom thereof extending outwardly therefrom, said base having a cavity therein adapted to receive a lens having a lenticular portion and a haptic portion and also having a bore extending through the center thereof for exposing said lens, first locking means integral with said base, a cover having a bore through the center thereof for exposing said lens, and being adapted to fit within said cavity in said base for fixing therebetween the position of a lens received in said cavity without contacting the lenticular portion of the lens, and second locking means integral with said cover and interconnectable with said first locking means to affix said base to said cover.

5. A lens storage device comprising a base having a bore extending through the center thereof and a cavity therein for receiving an intraocular lens having a lenticular portion and a haptic portion, said base having integrally therewith a first portion of a bayonet clamp, and a cover having a bore extending through the center thereof which is capable of communicating with said bore in said base to expose at least a portion of both sides of the intraocular lens and having an outer periphery which is substantially congruent with and received within the outer periphery of said cavity, said cover having integrally therewith a second portion of a bayonet clamp, said first and second portions of said bayonet clamp causing said cover to be connectable to said base.

6. A lens storage device as in claims 1, 2, 3, 4 or 5 wherein said central bores in said base and said cover are slightly sloped.

7. A lens storage device as in claims 1, 2, 3, 4 or 5 wherein said base and said cover fix the position of a lens placed therebetween by slightly frictionally engaging the lens.

8. A lens storage device as in claim 1 which further includes bayonet clamping means for causing said cylindrical first portion to interlock with said cylindrical second portion.

* * * * *